United States Patent [19]
Shaffer et al.

[11] Patent Number: 5,797,954
[45] Date of Patent: Aug. 25, 1998

[54] ACCESSING AND DEACCESSING TOOLS AND METHODS

[76] Inventors: Terry M. Shaffer, 7 Coralwind, Aliso Viejo, Calif. 92656; Jeanette Perlick, 5432 Kenilworth Dr., Huntington Beach, Calif. 92649; Robert J. Burns, 24341 DeLeon Dr., Dana Point, Calif. 92629-1609

[21] Appl. No.: 653,305

[22] Filed: May 24, 1996

[51] Int. Cl.$^6$ .................................................. A61B 17/00
[52] U.S. Cl. ................................................... 606/201
[58] Field of Search .......................... 606/1, 107, 108, 606/201–203; 604/179, 180, 308; 128/898

[56] References Cited

U.S. PATENT DOCUMENTS

| | | | |
|---|---|---|---|
| 1,561,116 | 11/1925 | Silliman | 606/201 |
| 2,234,961 | 3/1941 | Canada | 606/203 |
| 5,021,057 | 6/1991 | Byrne, Jr. | 606/201 |
| 5,601,596 | 2/1997 | Lam | 606/201 |

OTHER PUBLICATIONS

IInfection Control and Hospital Epidemology, Oct. 1993, vol. 14 No. 10 Port–a–Coth Needlestick Injuries.
Jun. 1996/Hospital Infection Control, p. 77, Double–deadly Needlestick transmits HIV and HCV.
Port–A–Cath Information (with Diagram).
Article: How to be ready for SMDA—pp. 4 and 5.
SHEA Annual Meeting Program; vol. 17, No. 5, Part 2 p. 27.
Infection Control & Hospital Edidemoloty; Medical News, Dec. 1993 Edited by Gina Pugliese, RN MS.
AJIC; Feb. 1996; vol. 24, No. 1;pp. 40 and 41.
Indirect Costs of Blookborne Pathogen Exposures;Summer1995 Lab Notes; by T.Rymer; pp. 1,2 & 3.
The Econimics of Needlestick Injuries; Spring 1994 Lab Notes; pp. 1, 2 & 3.
Infection Control & Hospital Epidemoloy; Puncture Injuries Due to Needles Removed from Intravenous Lines; Should the Source Patient Routinely Be Tested for Bloodborne Infections?pp. 325 thru 330; Jun., 1993.
Doyle Extractor Materials.

*Primary Examiner*—Michael Buiz
*Assistant Examiner*—William Lewis
*Attorney, Agent, or Firm*—John J. Connors; Connors & Assoc.

[57] ABSTRACT

Disclosed are tools and methods for assisting in the manual insertion of a needle into a medical device implanted under the skin of a patient and for assisting in the manual removal of the needle from this implanted medical device. The same tool may be used for both accessing and deaccessing the needle, or a special tool may be used for just assisting in the insertion of the needle into the implanted medical device. This special tool includes a holder section with a pair of fork elements spaced apart a distance which is slightly greater than the width of the implanted medical device. The tool for assisting in the manual removal of the needle from the implanted medical device includes an elongated body having a handle section and an enlarged guard section with an elongated slot extending from an edge of the guard section into the guard section, terminating at an internal portion of the guard section. The guard section of this tool is transparent, and preferably has indicia thereon which assist aligning the tool with the implanted medical device during needle accessing. The handle section and guard section may be detachable.

21 Claims, 8 Drawing Sheets

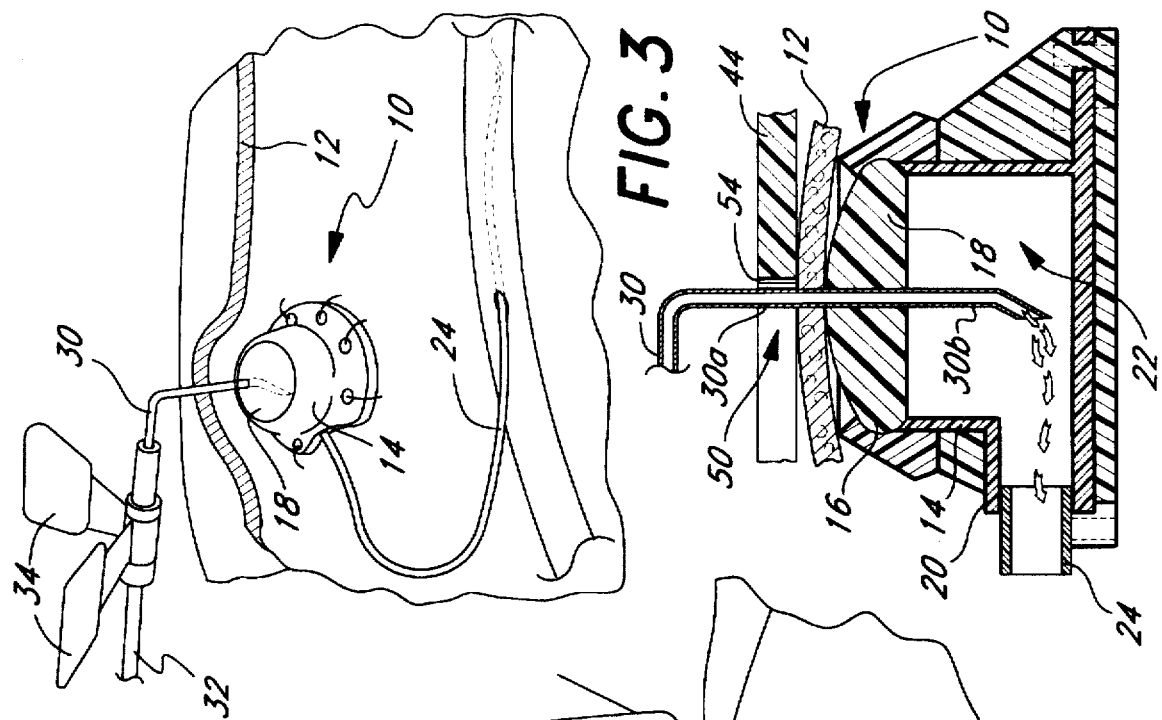
FIG. 2 (PRIOR ART)
FIG. 1 (PRIOR ART)
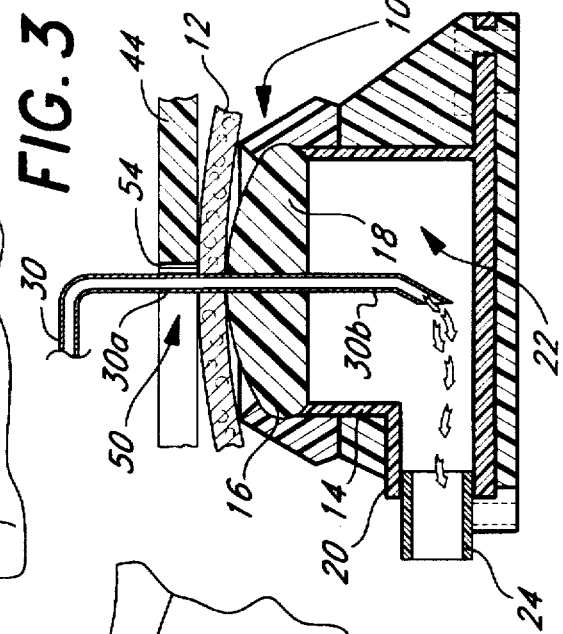
FIG. 3

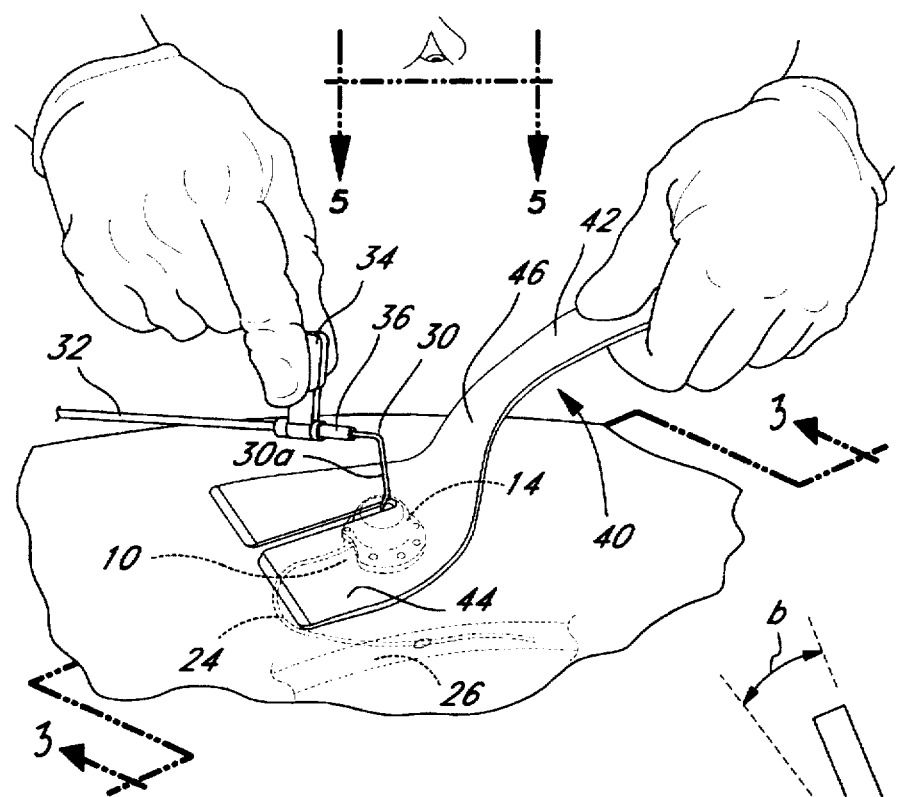
FIG. 4
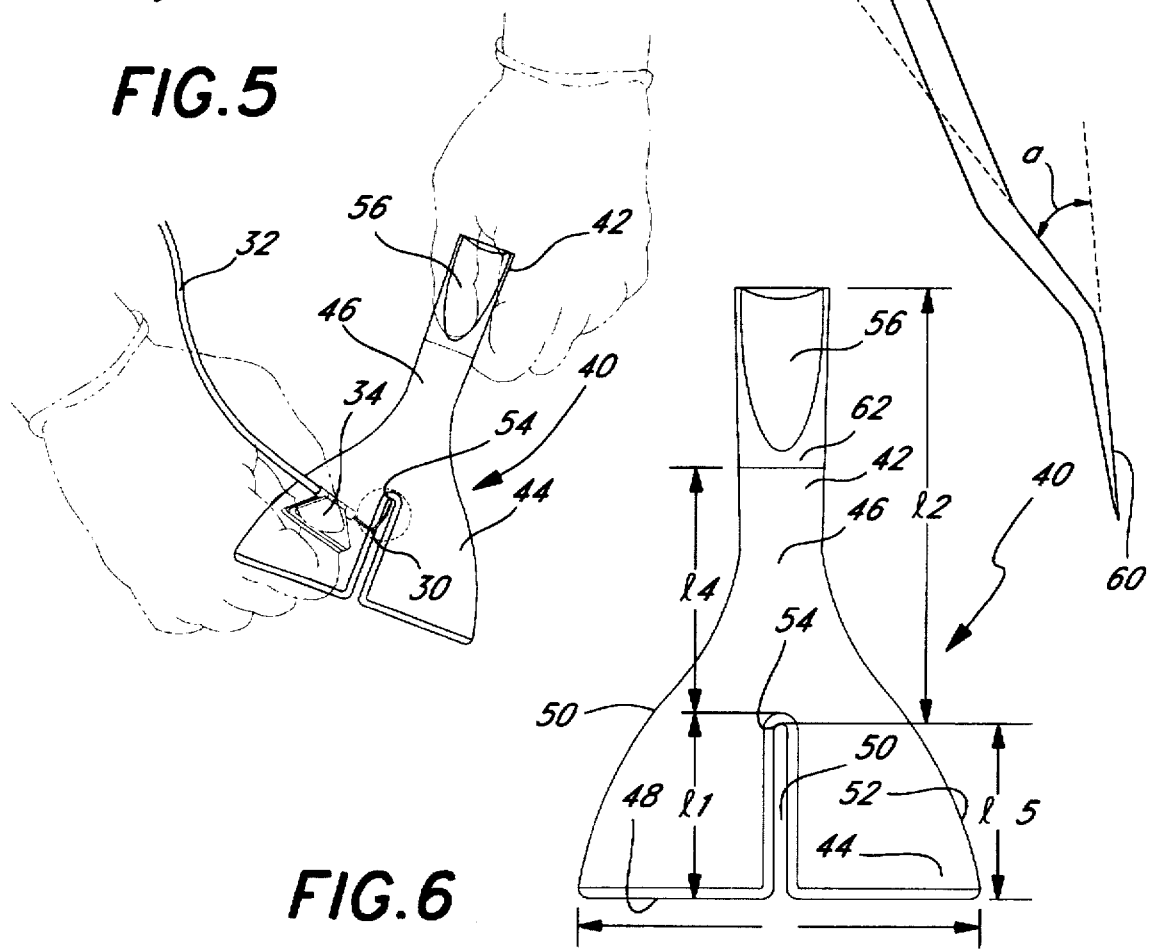
FIG. 5
FIG. 6
FIG. 7

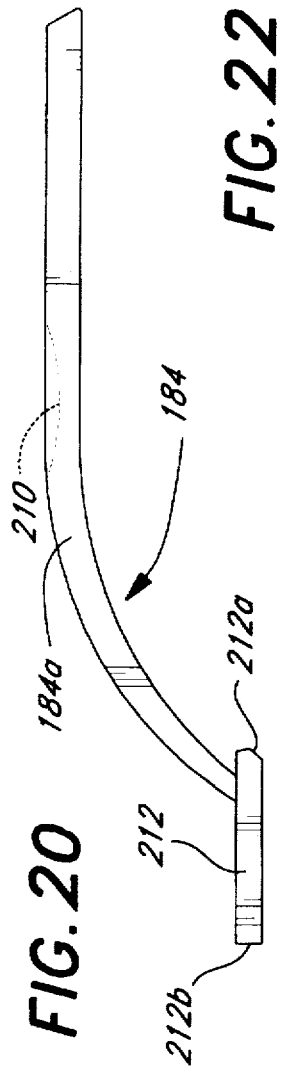
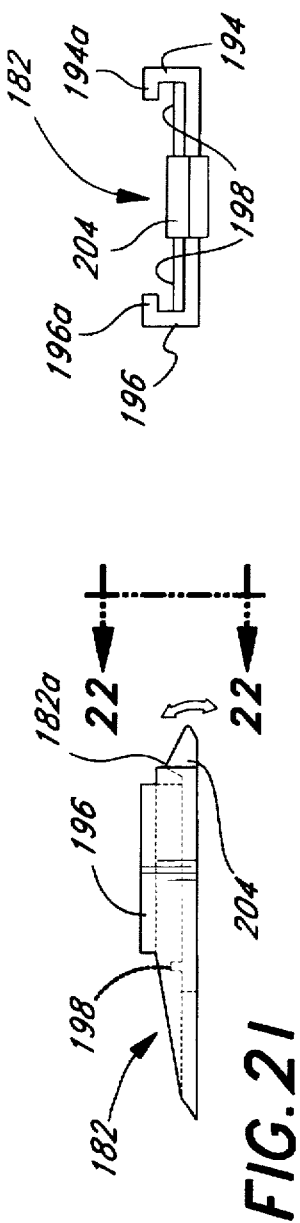
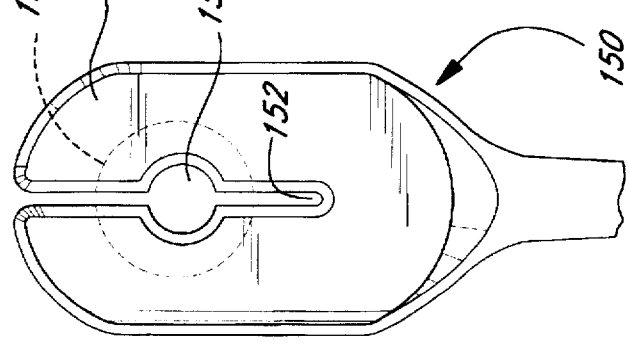
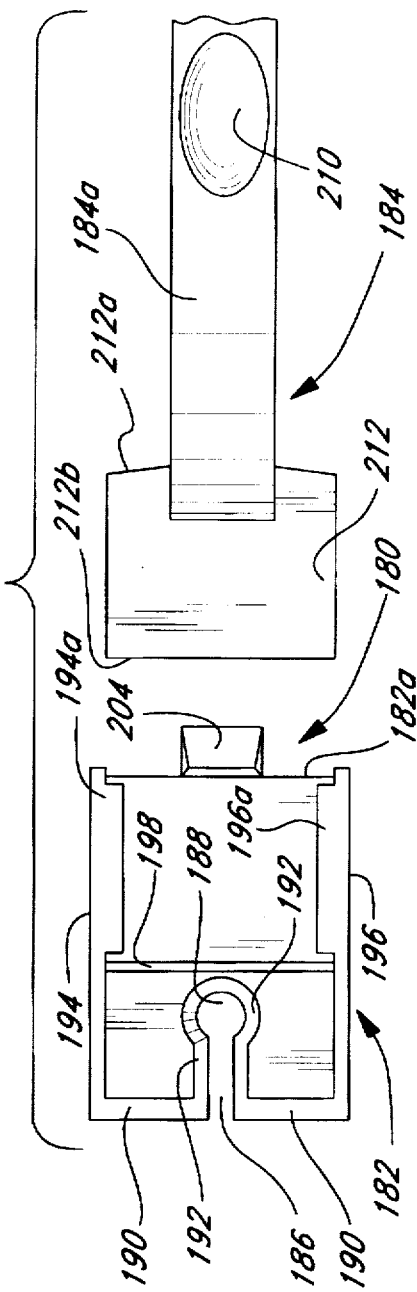

5,797,954

ACCESSING AND DEACCESSING TOOLS AND METHODS

BACKGROUND OF THE INVENTION

1. Field of the Invention

This invention relates to tools and methods for accessing and deaccessing a medical device implanted under the skin of a patient, and particularly tools and methods which reduce the risk of a nurse accidentally sticking herself or himself with a needle used with the implanted medical device.

2. Background Discussion

Implanted medical devices, such as vascular access devices, are commonly used to allow medication to be administered to patients. One such implant device is sold under the trademark "BardPort" by C. R. Bard, Inc. These devices include a housing enclosing a chamber which has an inlet covered with a silicone or latex seal. An outlet in communication with the chamber allows fluid in the chamber to flow through the outlet into a tube which, typically, is inserted into the vein of a patient.

These devices are accessed periodically by a nurse who inserts a needle through the patient's skin overlying the device and then into and through the seal. The nurse palpates, or feels, the device through the skin overlying the implanted device, and presses downward to locate the position of the implanted device. While holding or pressing against the device through the skin with one hand, the nurse with the other hand inserts the needle through the skin, and into and through the seal. Once properly inserted through the skin, the tip of the needle penetrates the seal and is lodged within the chamber. A "click" sound can sometimes be heard when the tip of the needle touches the bottom of the chamber, or the nurse can feel the tip contact the bottom of the chamber. Typically, the needle penetrates a depth of from about ¼ inch to about 1 inch. Medication now flows through the needle into the chamber and then out the outlet through the tube into the vein of the patient. Sometimes, however, the nurse, while attempting to introduce the needle into the seal of the implanted device, accidently sticks herself or himself with the needle. These accidental needle sticks occur while either accessing or deaccessing the implanted device with the needle.

Needle sticks occur most frequently while deaccessing the needle. The needle sometimes remains in the implanted medical device for several hours, and sometimes even for several days. These needles must be periodically flushed and removed from the device. The removal is accomplished by the nurse, with one hand, pressing against the skin overlying and around the device, and, with the other hand, grasping the needle and withdrawing it from the device. Frequently, there is an involuntary muscular recoil as the needle escapes from the implanted medical device as it is withdrawn. It is thought that this recoil is due to proprioceptive neuro-muscular activity. The recoil sometimes results in the nurse accidentally sticking a finger of the hand which is pressing against the skin adjacent to the implanted medical device. If the source patent has an infectious and or contagious disease such as disseminated TB, Hepatitis B or C, or is HIV positive or has Aids, the nurse may contract the disease directly from this needle stick.

After such a needlestick, even if the source patient has no communicable and/or infectious disease or condition identified at the time of the needlestick, the nurse must undergo intensive and expensive follow-up testing intermittently for up to 1 year. The source patient must be tested, if they consent, for infectious or communicable disease as set forth in the OSHA regulations and CDC (Center for Disease Control) recommendations, under Employee Exposure to Bloodborne Pathogens. The nurse must also be counseled as to certain restrictions in his or her own lifestyle, particularly sex practices, until his or her own freedom from communicable/infectious disease or condition is determined. This places an incredible strain on the nurse's marital relationships and lifestyle. The partner often demands that the nurse quit nursing rather than face the risks.

Needle sticks also occur while accessing the implanted device. The problem of contracting an infectious, contagious disease also is sometimes encountered. For example, the needle, which is typically sterile initially, has in some reported instances completely penetrated the finger of the nurse and entered the body of the patient. The now contaminated needle can only be removed by withdrawing it from the patient's body into and through the nurse's finger, possibly infecting the nurse.

Recent guidelines promulgated by the CDC prohibits medical acts which require manipulating needles using both hands in the act, or any other technique that involves directing the point of a needle toward any part of the Health Care Workers body. Under the current protocols for using the implanted device, the nurse's hand which secures the implanted device in place during accessing and deaccessing is always in direct line with the needle during accessing, and also in line with the needle tip during deaccessing when one considers the frequency of the known recoil phenomenon.

The problem of needle sticks while deaccessing the needle has been recognized by workers at the University Hospital in Antwerp, Belgium, who published an article in Infection Control and Hospital Epidemiology, Volume 14, No. 10 (October 1993). In this article it is suggested to use a tool, rather than the nurse's hand, to hold the implanted device during removal of the needle. The suggested tool includes a guard with a slot in it. The guard has a relatively small area. It appears to be less than 1 square inch, and it appears to be made of an opaque material. There is a short handle attached to the guard used to grasp the tool which does not permit the hand of the nurse to be located far enough away from the needle to insure avoiding needle sticks if a recoil occurs.

SUMMARY OF THE INVENTION

It is the objective of this invention to provide tools and methods which allow a nurse to access and deaccess safely a needle used with an implanted medical device. This invention has several features, no single one of which is solely responsible for its desirable attributes. Without limiting the scope of this invention as expressed by the claims which follow, its more prominent features will now be discussed briefly. After considering this discussion, and particularly after reading the section entitled, "DETAILED DESCRIPTION OF THE PREFERRED EMBODIMENTS," one will understand how the features of this invention provide its benefits, which include low cost manufacture, simplicity of use, and, most importantly, nurse and patient safety by avoiding accidental needle sticks and the ensuing medical costs and risks such as, for example, loss of health or life, ability to work, and sometimes spousal support.

The first feature of the tool of this invention is that it may be used for assisting in both accessing and deaccessing a needle used with a medical device implanted under the skin of a patient. In one embodiment it has the general configuration of a spatula and it includes an elongated body having a handle section and an enlarged guard section. There is an elongated slot extending from an edge of the guard section into the guard section, terminating at an internal portion of the guard section. The guard section has an area in excess of 1.25 square inches, typically the area is from about 1.25 square inches to about 18 square inches. This relatively large guard area prevents the patient from being stuck with the needle, if there is a recoil during removal of the needle from the implanted medical device.

The second feature is the dimensions and other physical characteristics of the guard section. The guard section has a forward edge terminating at opposed ends and side edges at each opposed end which extend rearward to the handle section. The guard section has a floor including the forward edge, opposed sides, and a rear end. There is a raised rear wall connected to the rear of end of the floor, and a pair of raised side walls, each connected to one side of the floor. Preferably, the side walls taper down from their highest distance above the floor near the rear end to essentially level with the floor near the forward edge. The forward edge has a length of from about 1 to about 6 inches. The side edges have a length of from about 0.5 to about 3 inches. The guard section has a smooth, generally planar underside surface and a thickness of from 1/32 to 3/16 inch. The walls have a maximum height of about 1/4 inch.

The third feature is the dimensions and other physical characteristics of the slot. The slot extends from an edge of the guard section inward a distance in excess of 1/4 inch, preferably having a length of from about 0.25 to about 3 inches, and it has a width that is slightly broader than the diameter of the needle, typically from about 1/16 to about 1/4 inch. Preferably, the slot is at a right angle with respect to the forward edge, and the slot and the handle section are in substantial alignment with each other, both lying along a common longitudinal axis. Preferably, the minimum distance between the slot and a side edge is about 1 inch and the maximum distance between the slot and a side edge is about 3 inches. The elongated slot preferably has tapered edges. These tapered edges assist in removal of the needle from the implanted medical device.

The fourth feature is that the guard section is made of a transparent material. In most instances the entire tool is injected molded from a polymeric material such as, for example, polycarbonate, sold under the trademark LEXAN by General Electric, Inc. Because the guard section is transparent, the nurse may more easily align the tool with the implanted medical device. This is especially advantageous during accessing the implanted device. In one embodiment especially designed to assist in accessing the implanted device, the slot has along it's length an enlarged open portion with an area in excess of 0.0036 square inch. Preferably, the open portion is circular having a diameter greater than 1/16 inch, typically from 1/8 to 1/4 inch. The nurse inserts the needle through this enlarged open portion when accessing the implanted medical device. Preferably, the enlarged open portion is about midway between the forward edge and the bite of the slot. Preferably, there are indicia on the guard section which assist the nurse in aligning the guard section with the implanted medical device during accessing. For example, there may be a pair of marks on the guard disposed along the slot which are spaced apart a distance approximately equal to the width of the implanted medical device, typically from 3/4 to 1 1/2 inch. Alternately, the indicia may be at least partially encompassing the enlarged open portion along the slot. For example, the indicia may be a circle with its center coincident with the center of the enlarged circular open portion.

The fifth feature is that the tool is designed to enable the nurse to keep his or her hand a safe distance away from the needle during removal of the needle from the implanted device. The tool typically has a length of from 4 to 11 inches, and the handle section typically has a length of from 3 to 8 inches. The handle section has an elongated depression therein extending lengthwise along this handle section into which the thumb is placed during use. This depression provides a lever platform to enhance manipulative control of the tool. Thus, even someone with poor finger dexterity may easily manipulate the tool of this invention. In the preferred embodiment of this invention, the handle section has a marker on it indicating that the hand of the nurse should be behind this marker. The marker is at a distance to position the hand of the nurse at least 3 inches away from the needle during use. The handle section may include an intermediate neck section, and the guard section is joined to the intermediate neck. The handle section and the intermediate neck are at an acute angle of from 0 to 20 degrees, and the intermediate neck section and the guard section are at an acute angle of from 10 to 40 degrees.

The sixth feature is that a special tool is provided for assisting in the manual insertion of a needle into the implanted medical device of a predetermined width. This tool includes a handle section and a holder section, with the holder section having a pair of fork elements spaced apart a distance which is slightly greater than the width of the medical device. Typically, this distance is from about 1/2 inch to about 2 inch. The fork elements are of equal length, each having a length of from about 0.5 inch to about 3 inch. The holder section has a length of from 0.5 to 3 inches and the handle section has a length of from 3 to 8 inches. The longitudinal axis of the handle section bisects the holder section, with each fork element being equidistance from the longitudinal axis. The holder section has a smooth, generally planar underside surface, and the handle section has a marker thereon indicating that the hand of the nurse should be behind this marker.

The seventh feature is that the handle section and guard section may be detachable, enabling the guard section to be discarded after use and the handle section reused. There is a locking mechanism that engages the handle section upon inserting the handle section into a track on the guard section and a manually releasable element that upon being released allows the handle section to be detached from the guard section.

This invention also includes a number of methods for accessing and deaccessing the implanted medical device. The first method is for manually removing a needle from a medical device implanted under the skin of a patient. It includes the following steps:

(a) grasping with the one, typically the nondominant, hand a handle section of a tool having a guard section having an area in excess of 1.25 square inches and a slot therein, (b) sliding the slot along the needle to bring the guard section into an overlying relationship with the implanted medical device, (c) maintaining the one hand a minimum distance away from the needle of at least 3 inches and exerting sufficient pressure to stabilize the guard area holding the implanted medical device preventing said device from moving, (d) with the other, typically the dominant hand, withdrawing the needle free of the implanted medical device. The deaccessing tool discussed above is used in performing this method.

The second method is for manually inserting a needle into a medical device implanted under the skin of a patient. It includes the following steps:
  (a) grasping with one hand, typically the non-dominant hand, a tool with a holder section and a handle section, and holding a tool by the handle section and pressing the holder section against the skin overlying the medical device, and
  (b) gripping the needle with the other hand, typically the dominant hand, and inserting said needle through said skin into the medical device, and
  (c) maintaining said one hand a distance of at least 3 inches away from the needle as said needle is inserted into the medical device.

Either the tool discussed above which is designed especially for accessing the implanted medical device or the tool for deaccessing the needle may be used to conduct the second method. It is preferable that the guard sections of these tools be transparent and have indicia thereon which assist the nurse aligning the slot with the implanted device. These tools with transparent guard sections and indicia thereon may be used for both accessing and deaccessing the needle.

DESCRIPTION OF THE DRAWING

The preferred embodiments of this invention, illustrating all its features, will now be discussed in detail. These embodiments depict the novel and non-obvious accessing and deaccessing tools and methods of this invention as shown in the accompanying drawing, which is for illustrative purposes only. This drawing includes the following figures (FIGS.), with like numerals indicating like parts:

FIG. 1 is a perspective view illustrating a nurse being accidentally stuck with a needle that is being removed from an implanted medical device in the conventional manner.

FIG. 2 is a perspective view showing the needle inserted into an implanted medical device in the conventional manner.

FIG. 3 is a cross-sectional view taken along line 3—3 of FIG. 4.

FIG. 4 is a perspective view illustrating using the tool of this invention to safely remove a needle from an implanted medical device.

FIG. 5 is a plan view taken along line 5—5 of FIG. 4.

FIG. 6 is a plan view of the tool of this invention.

FIG. 7 is a side elevational view of the tool of this invention.

FIG. 14A is a top plan view of a sixth embodiment of the tool of this invention, showing a modified guard section similar to the guard shown in FIG. 14, except including an opening along the slot for providing easy access to the needle when inserting the needle into the implanted device.

FIG. 19 is a plan view of the tool shown in FIG. 18 showing the handle and guard sections detached.

FIG. 20 is a side elevational view of the detached handle section illustrated in FIG. 18.

FIG. 21 is a side elevational view of the detached guard section illustrated in FIG. 18.

FIG. 22 is a sectional view taken along line 22—22 of FIG. 21.

DETAILED DESCRIPTION OF THE PREFERRED EMBODIMENTS

Prior Art

Figure 8:
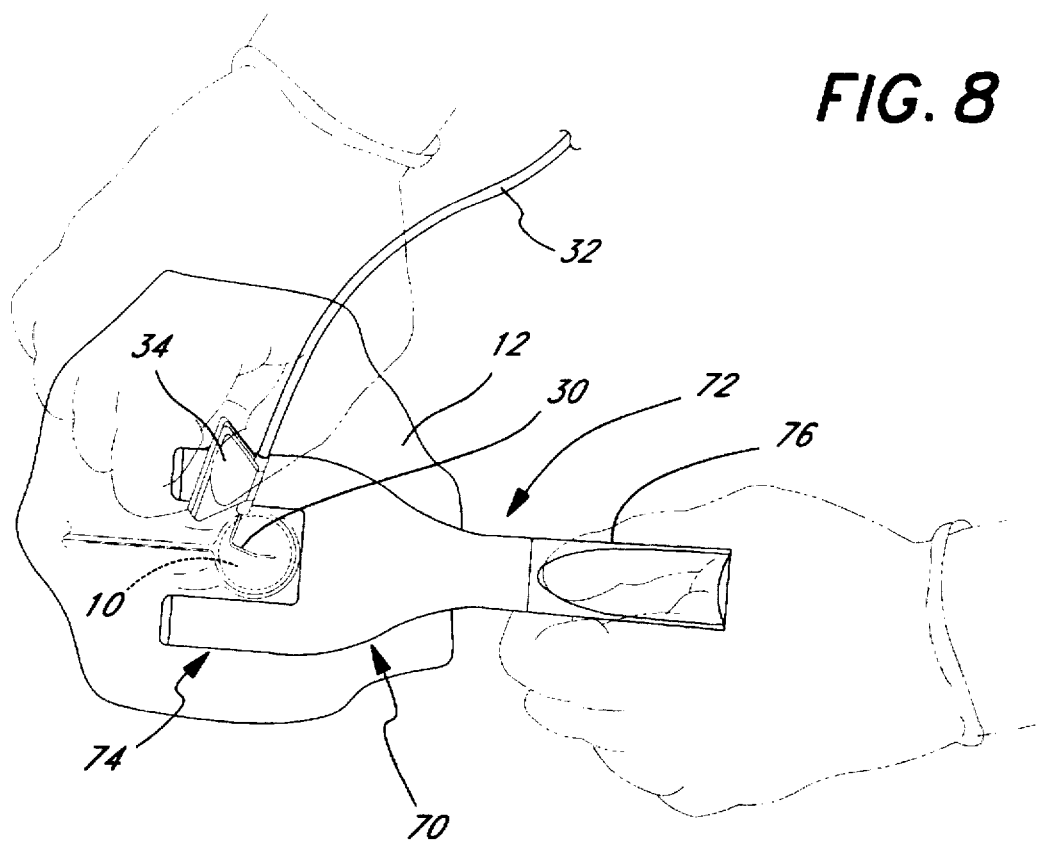
FIG. 8 is a plan view illustrating a nurse using an accessing tool of this invention to hold steady an implanted medical device while a needle is being inserted through the patient's skin into the implanted medical device.

As illustrated in FIGS. 1 and 2 a conventional vascular access device 10 has been implanted in the conventional manner under the skin 12 of a patient. As best shown in FIG. 3, this vascular access device 10 includes a housing 14 having an inlet 16 sealed by a latex seal 18. There is an outlet 20 in the device 10 remote from the inlet 16 with a fluid retention chamber 22 between the inlet and outlet. A tube 24 connected to the outlet 20 is inserted using a catheter (not shown) into a vein 26 of the patient.

A non-coring needle 30 is employed to administer medication through the vascular access device 10. The needle 30 has a generally 90 degree angle bend with one end of the needle being in communication through a tube 32 with the medication (not shown). A pair of flexible wings 34 extend outward from a hub 36. The nurse grasps these wings 34 when inserting or removing the needle 30 from the vascular access device 10. The shaft 30a of the needle 30 extends through the patient's epidermal layer of skin 12 and penetrates the seal 18, with the tip 30b of the needle entering the chamber 22. The medication flows through the needle 30 into the chamber 22 and then out the chamber through the tube 24 into the patient's vein 26. When the needle is removed as illustrated in FIG. 1, there sometimes occurs an involuntary recoil of the nurse's hand as she or he withdraws the needle from the seal 18 and skin 12. This often happens when exudate from the wound produced by insertion of the needle 30 hardens or the needle is left in the device for a number of days. The recoil many times results in the nurse being stuck with the needle. Such a needle stick can result in infection with AIDS, Hepatitis B, or other infectious diseases.

First Embodiment

In accordance with this invention, a tool 40 is employed to remove safely the needle 30 from the vascular access device 10. As best illustrated in FIGS. 4 through 7, this tool 40 includes a handle section 42 and an enlarged guard section 44 connected by an intermediate neck section 46. The intermediate neck is at an acute angle of about 35 degrees with respect to the guard section 44, and at an acute angle of about 15 degrees with respect to the handle section 42. The area of the guard section 44 is in excess of 1.25 square inches, and in the embodiment illustrated has an area of 3–4 square inches. The guard section 44 has the general configuration of a spatula with the guard section 44 providing a shield which covers or overlies the skin area adjacent the vascular access device 10. The tool 40 includes a forward edge 48 which preferably is beveled or tapered. At the opposed ends of this forward edge 48 are side edges 50 and 52 which extend rearward toward the handle section 42. There is an elongated slot 50 which extends from the forward edge 48 rearward towards the handle section 42 and terminates at a bite 54 which acts as a stop.

As best shown in FIGS. 4 and 5, the nurse grasps the handle section 42 with the left hand, if their dominant hand is the right hand, placing the thumb in a thumb depression 56 (FIGS. 5 and 6) in the handle section. The tool 40 is positioned next to the needle 30, and moved towards the needle, sliding the slot 50 along the shaft 30a of the needle until the shaft abuts the bite 54 of the slot. The nurse presses gently downward against the surface of the skin 12 with the generally flat, smooth underside 60 (FIG. 7) of the guard section 44, pressing against the surface of the skin to prevent the vascular access device 10 from moving while the needle 30 is being slowly lifted from the device while maintaining the needle generally at a right angle with respect to the seal 18. With the dominant right hand, the nurse grasps the wings 34, pressing them together, and withdraws the needle 30 outward and away from the device 10 with a smooth steady motion. If there is a recoil, the guard section 44 prevents the needle 30 from sticking the patient and, because the left hand is now remote from the vascular access device 10, being at least 3 inches away from the needle when lodged in the device 10, it is virtually impossible for the nurse to stick him or herself with the needle 30 upon withdrawing the needle from the device. Although the thumb depression 56 serves to position the left hand of the nurse a safe distance away from the needle 30 lodged in the device 10, a mark 62 (FIG. 6) may also be used to indicate the proper hand position. If the thumb depression 56 is eliminated, such a mark 62 indicates to the nurse that his or her hand should remain placed behind this mark on the side of the mark furthest away from the needle 30.

The tool 40 preferably is made of a transparent material such as polycarbonate plastic which enables the tool to be injection molded, and therefore inexpensively mass produced. The tool 40, particularly when the guard section 44 is made of a transparent material, may be used to insert the needle into the vascular access device 10. In this case of accessing the device 10, the nurse first locates the implanted device 10 by palpating the skin 12, and then tool 40 is placed over the implanted device and pressed downward against the skin 12 overlying the device 10, and the needle is inserted through the slot 50 into the skin 12 and seal 18.

The dimensions of this tool are very important to ensure the proper safe performance of the device. These dimensions are set forth in the following table with references to FIG. 6.

TABLE I

| ITEM | DIMENSION RANGE |
|---|---|
| $l_1$ | 0.5 inch–3 inch |
| $l_2$ | 3 inch–8 inch |
| $l_3$ | 1 inch –6 inch |
| $l_4$ | .5 inch–5 inch |
| $l_5$ | 0.25 inch–2 13/16 inch |

Second Embodiment

Figure 9:
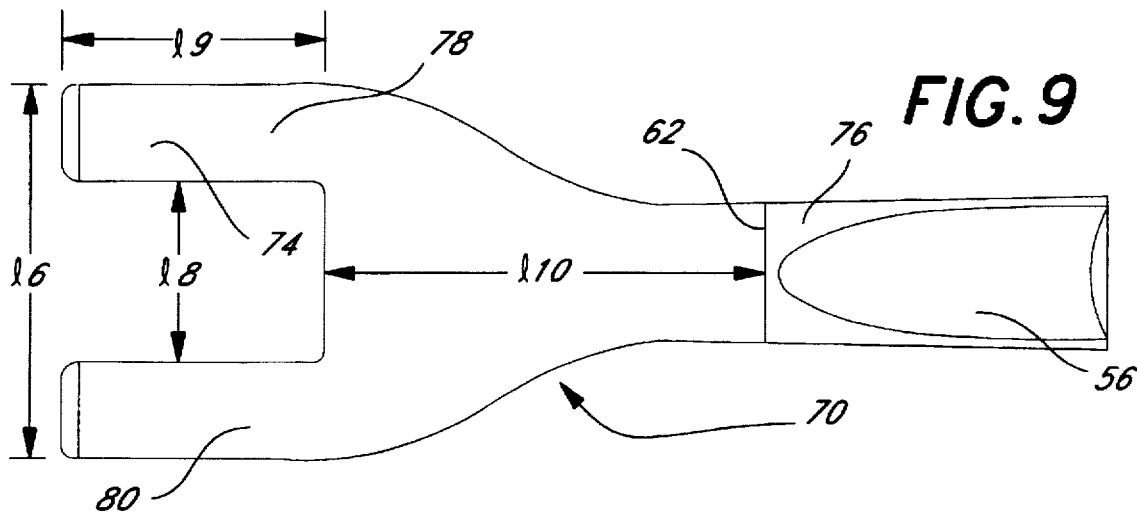
FIG. 9 is a plan view of the accessing tool of this invention.
Figure 10:
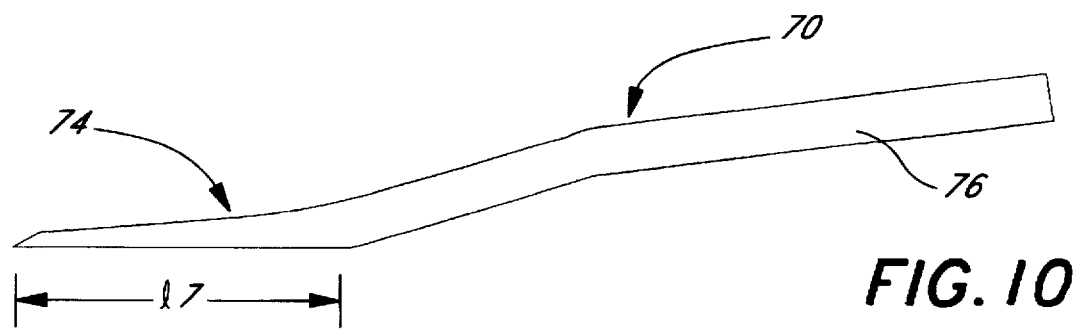
FIG. 10 is a side elevational view of the accessing tool of this invention.

Also in accordance with this invention, there is provided as shown in FIGS. 8 through 10 a specially designed tool 70 for safely inserting the needle 30 into the vascular access device 10. Although this procedure is not as dangerous, because the needle 30 is ordinarily sterile, a needle stick may under some circumstances cause transmission of disease. Thus, it is highly desirable to avoid a needle stick when accessing the implanted device 10.

The accessing tool 70 comprises an elongated body 72 having a holder section 74 attached to a handle section 76. The holder section 74 includes two outwardly extending fork elements 78 and 80 which are spaced apart a distance equal to the width of the vascular accessing device 10. Preferably there is a thumb depression 56 in the handle similar to that illustrated in connection with the tool 40 to insure maintaining the safe distance away from the needle 30 as it is inserted into the implanted device 10.

As best shown in FIG. 8, the nurse holds the accessing tool 70 in the left hand while grasping the wings 34 of the needle 30 with the right hand. The nurse pushes the tip 30b of the needle 30 through the layer of skin 12 into and through the latex seal 18. Simultaneously, the holder section 74 is placed over the skin, with the forks 78 and 80 straddling the vascular accessing device 10, enabling the nurse to hold the device steady and virtually immovable while the needle 30 is being inserted into the device.

The important dimensions of the accessing tool are set forth in the following table with reference to FIGS. 9 and 10.

TABLE II

| ITEM | DIMENSION RANGE |
|---|---|
| $l_6$ | 1 inch–6 inch |
| $l_7$ | 0.5 inch–3 inch |
| $l_8$ | ½ inch–2 inch |
| $l_9$ | ½ inch–3 inch |
| $l_{10}$ | 1 ½ inch–5 inch |

Third Embodiment

Figure 11:
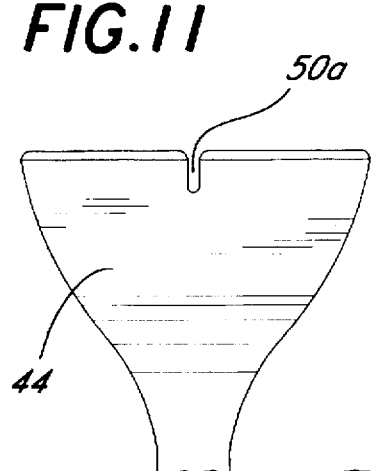
FIG. 11 is a fragmentary plan view of a second embodiment of the tool of this invention, showing a modified guard section.

As illustrated in FIG. 11, the tool 40 has been modified so that the length of slot 50a is substantially shorter than shown in FIG. 6. The use of such a short slot 50a may be desirable in certain applications, such as deaccessing a difficult to remove embedded needle. The shorter slot 50a may be used as a wedge to pry the needle away from the patient skin.

Fourth Embodiment

Figure 12:
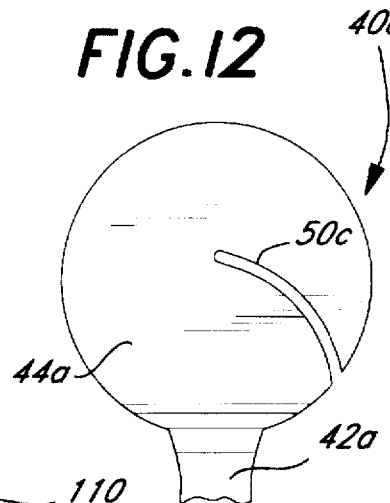
FIG. 12 is a fragmentary plan view of a third embodiment of the tool of this invention, showing a modified guard section for a right handed nurse.
Figure 13:
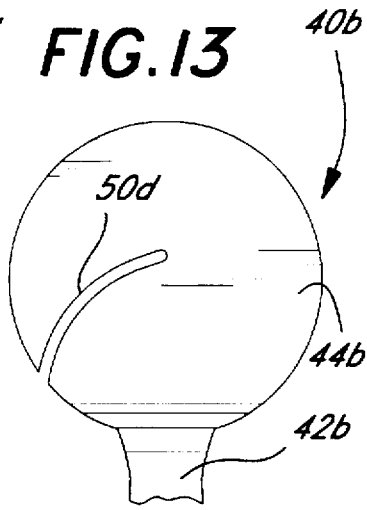
FIG. 13 is a fragmentary plan view of a fourth embodiment of the tool of this invention, showing a modified guard section for a left handed nurse.

The fourth embodiment includes a tool 40a with a circular shaped guard section 44a. In FIG. 12, the slot 50c is curved inward from a portion of the edge of the guard section 44a near the handle section 42a. This tool 40a is used with the left hand. This fourth embodiment also includes a tool 40b with a circular shaped guard section 44b. In FIG. 13, the slot 50d is curved inward from a portion of the edge of the guard section 44b near the handle section 42b. This tool 40b is used with the right hand.

Fifth Embodiment

Figures 14, 15:
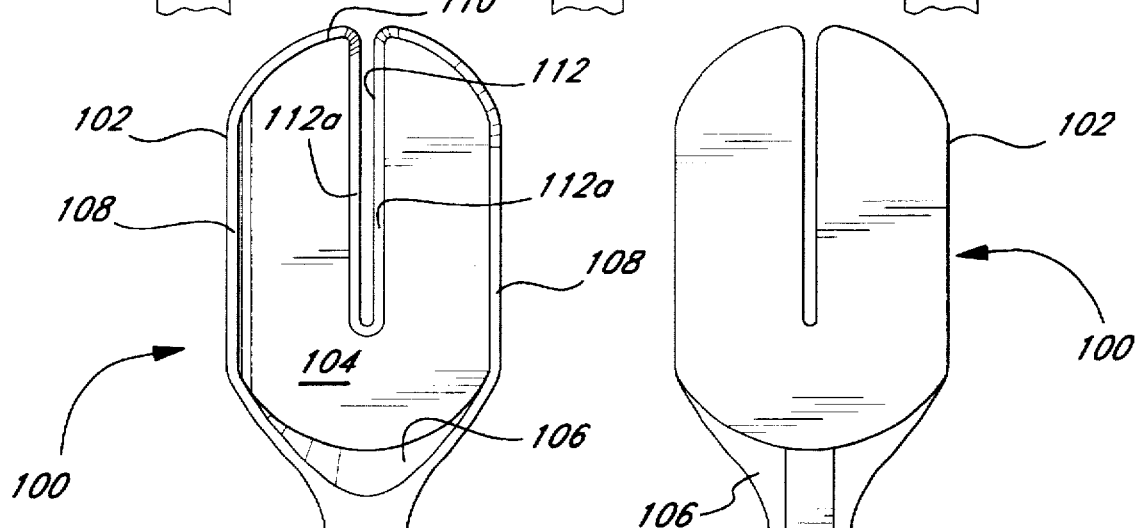
FIG. 14 is a top plan view of a fifth embodiment of the tool of this invention, showing a modified guard section with a sunken floor.
FIG. 15 is a bottom plan view of the fifth embodiment of the tool of this invention shown in FIG. 14.

As illustrated in FIGS. 14 and 15, the fifth embodiment includes a tool 100 with a modified guard section 102. The guard section 102 employs a recessed floor 104. This floor 104 has a wall 106 attached to its rear end and a side wall 108 along each side edge of the floor. The side walls 108 merge with the rear wall 106 to partially enclose the floor. Only the forward edge 110 of the floor 104 is free for use in accessing or deaccessing the needle 30. The side walls 108 preferably taper downward from their highest elevation at the rear wall 106 towards the forward edge 110.

There is a slot 112 extending from the forward edge 110 towards the central section of the floor. The edges 112a of the slot 112 and the forward edge 110 are beveled or tapered. Such a taper assist the nurse in wedging the tool 100 underneath the needle 30 inserted and sometimes flush against the skin 12. When the needle is difficult to remove, these tapers edges of the forward edge and slot serve as a wedge to lift the needle up slightly off the surface of the skin.

Sixth Embodiment

Figure 16:
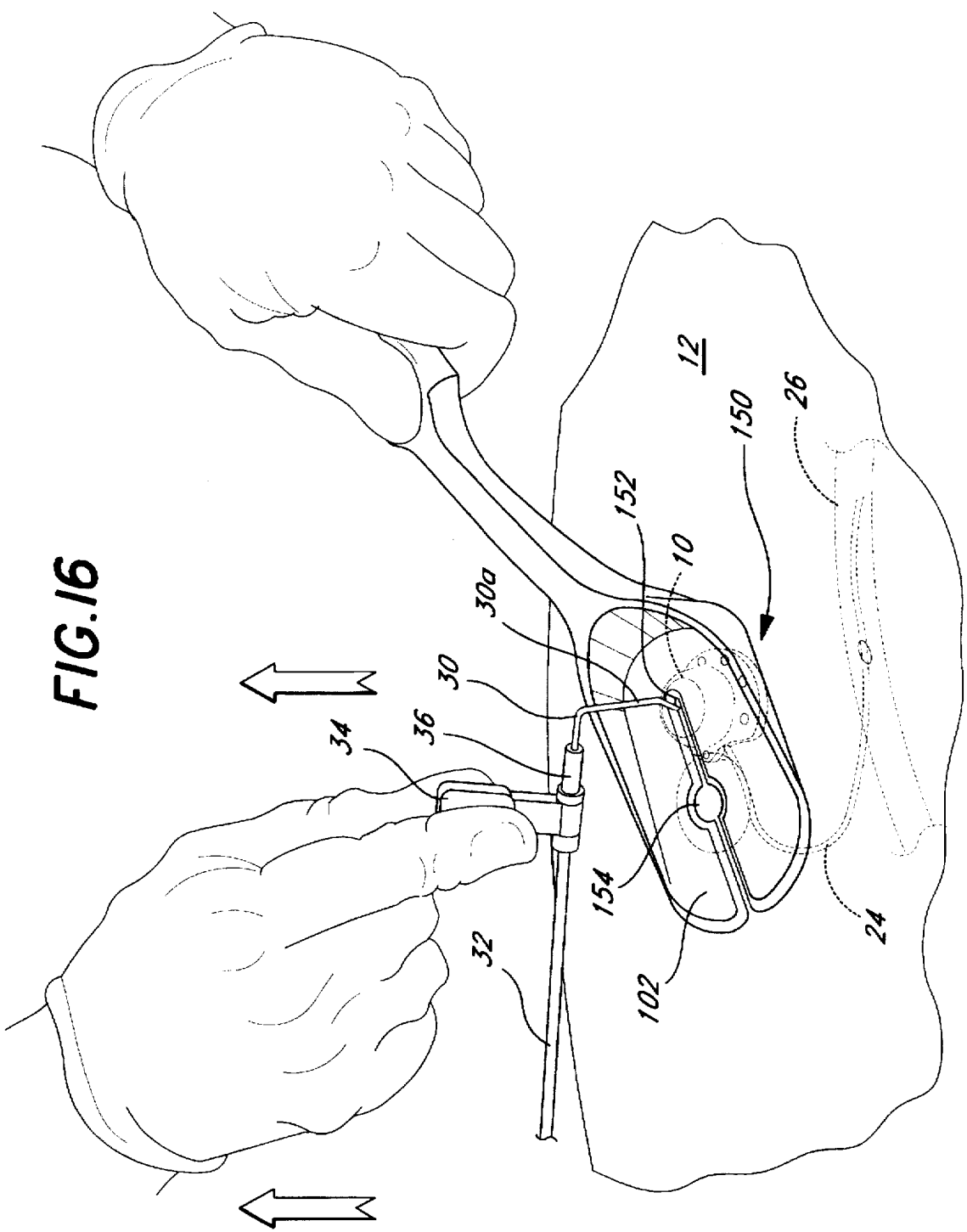
FIG. 16 is a perspective view illustrating a nurse using a tool similar to that shown in FIG. 14A to remove a needle from an implanted medical device, except modified to facilitate using the tool for both accessing and deaccessing the needle.
Figure 17:
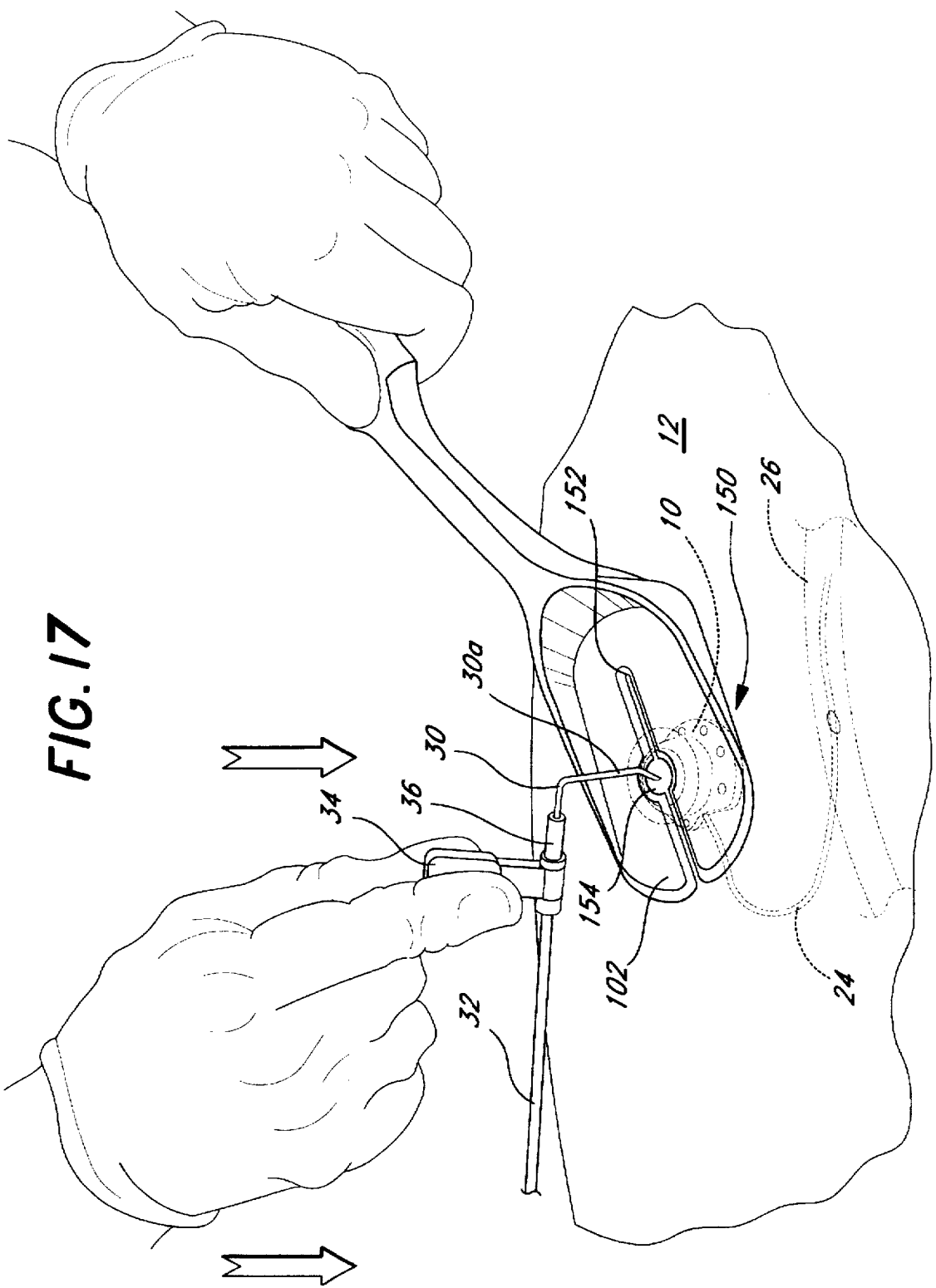
FIG. 17 is a perspective view similar to that shown in FIG. 16 where the nurse is using the tool shown in FIG. 16 to access a needle into an implanted medical device.
Figure 18:
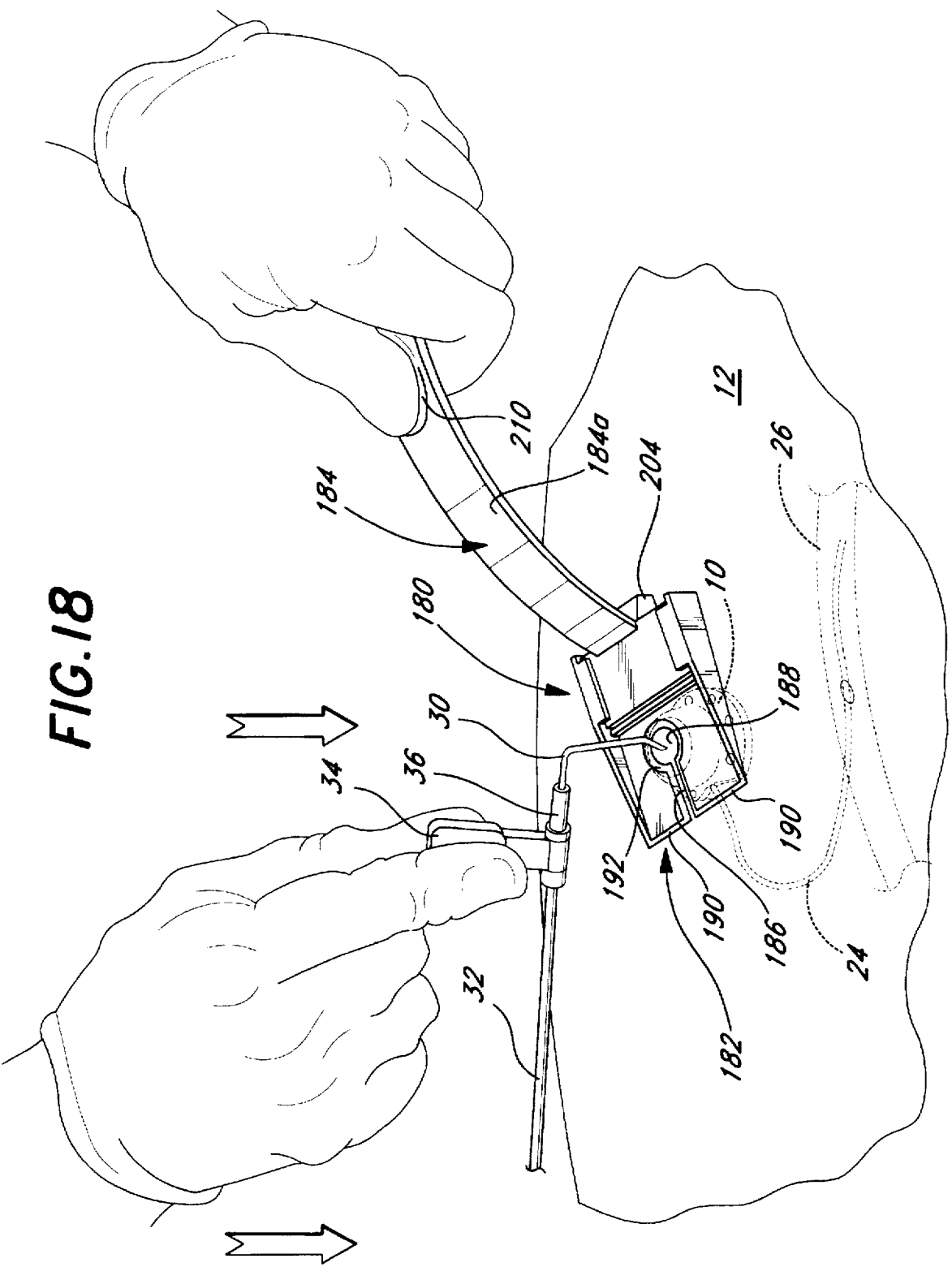
FIG. 18 is a perspective view of a seventh embodiment of the tool of this invention which is similar to that shown in FIG. 17, except modified to so that the handle and guard sections are detachable.

As depicted in FIGS. 14A, and 16 and 17, the tool 100 has been modified to better enable it to be used for both accessing and deaccessing the needle 30. The principal difference between the tool 100 and the sixth embodiment of this invention, the tool 150, is that the slot 112 has along its length about midway between the forward edge 110 and the bite 152 of the slot, an enlarged open portion 154 encircled by a dotted circular red line 156. This circular line 156 has its center coincident with the center of the enlarged open portion 154. The guard section 102 of the tool 150 is made of a transparent material.

As illustrated in FIG. 16, the tool 150 is used to deaccess the needle already inserted into the device 10 by positioning the guard section 102 so that the needle shaft 30 a abuts the bite 152 of the slot 112. As discussed above, the nurse then grasps the wings 34 of the needle 30 and withdraws the needle from the vascular accessing device 10. As illustrated in FIG. 17, to use this same tool 150 for accessing the needle 30, the nurse first palpates the skin 12 to locate the device 10. Then the nurse positions the tool 150 with the guard overlying the implanted device. Because the guard section 102 is transparent, this is more readily accomplished than when using a guard of opaque material. The nurse uses the circular dotted red line as a sighting mechanism, bring the guard section into a position where the center of the implanted device 10 is coincident with the center of the enlarged open portion 154. The nurse then directs the needle through the open portion 154, and into the skin and device. The needle 30 is aligned at an angle of about 90 degrees with respect to the surface of the skin 12. Because the open portion 154 is substantially larger than the diameter of the needle 30, the nurse will be able to move the needle through the open portion 154 without touching the guard member, thereby avoiding contaminating the needle. Typically, the area of the open portion 154 is greater than 0.0036 square inch, and is circular having a diameter greater than 1/16 inch.

Seventh Embodiment

The seventh embodiment depicted in FIGS. 18 through 22 illustrate an accessing and deaccessing tool 180 which has a guard section 182 detachably connected to a handle section 184. Preferably, the guard section 182 is made of an inexpensive, transparent material, and is sterile prior to use and may be discarded after use. The handle section 184 preferably is made of an opaque, durable material and may be reused several times.

The handle section 184 has an elongated handle 184a with a thumb depression 210 in an intermediate portion. A tongue 212, integral with the forward end of the handle 184a, and having a generally rectangular configuration with a width slightly less than the width of the guard section, serves as the connector for attaching the handle section 184 to the guard section 182. The back end 212a of the tongue 212 is chamfered, and as will be discussed in greater detail subsequently, interacts with a tab 204 on the guard section 182 when the handle and guard sections engage.

The guard section 182 (FIG. 18) is similar to the guard section 102 (FIG. 16) of the tool 150. It has an elongated slot 186 extending inward that terminates in an enlarged circular opening 188 that is aligned with the vascular access device 10 when the tool is to be used to access the vascular access device. The leading edges 190 and sides 192 of the slot 186 and opening 188 are tapered to assist in slipping the guard section 182 under a needle 30 in the vascular access device 10 when the tool 180 is used for deaccessing the needle 30. The lateral sides 194 and 196 (FIG. 22) are raised and each has an inwardly directed lip 194a and 196a, respectively. These lips 194a and 196a serve as tracks for holding the handle section 184 upon attaching the handle section to the guard section 182. There is a stop member 198 (FIG. 19) between the inward ends of the lips 194a and 196a and the circular opening 188 that limits the inward movement of the handle section 184.

As best illustrated in FIGS. 19 and 22, at the rear 182a (FIG. 19) of the guard section 182 the tab 204 that engages the handle section 184 upon inserting the tongue 212 of the handle section under the tracks provided by the lips 194a and 196a. This tab 204, which is manually released by depressing it, is integral with the rear 182a of the guard section 182 and pivots along a hinge formed along the line of connection with the rear 182a of the guard section 182. When depressed, the tab 204 is moved downward to allow the tongue 212 to be slipped beneath the lips 194a and 196a until the forward end 212b of the tongue engages the stop member 198. Upon release, it springs back into its normal position depicted in solid lines in FIG. 21 to grasp the chamfer edge 212a of the tongue 212 of the handle section 184. To disconnect the handle section 184, the tab 204 is manually depressed and the handle section is simply pulled away from the guard section 182, with the tongue 212 sliding along the lips 194a and 196a until clear. Thus, the tab 204 and chamfer edge 212a provide a locking mechanism which is manually released.

General Procedures

Conventional aseptically clean techniques are followed in using the tools and methods of this invention, and the needle 30 is flushed with saline and Heparin solutions to avoid clogging. Clean or sterile rubber gloves should be worn when accessing and deaccessing the needle 30, and all used needles 30 are disposed of in sharps safety containers.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention:

What is claimed is:

1. A method for manually removing a needle from a medical device implanted under the skin of a patient, including grasping with one hand a handle section of a tool having a guard section having an area in excess of 1.25 square inches and a slot therein, sliding the slot along the needle to bring the guard section into an overlying relationship with the implanted medical device, maintaining said one hand a minimum distance away from the needle of at least three inches, and with the other hand withdrawing said needle free of the implanted medical device.

2. The method of claim 1 where the guard section is made of a transparent material.

3. The method of claim 1 where the tool includes an elongated body having the handle section attached to the guard section, said guard section having a forward edge terminating at opposed ends, side edges at each opposed end which extend rearward to said handle section, and an elongated slot which extends from the forward edge rearward towards said handle section, said forward edge having a length of from 1 to 6 inches, said side edges having a length of from 0.5 to 3 inches, and said slot having a length of from 0.25 to 3 inches.

4. The method of claim 1 where said slot has a width that is slightly broader than the diameter of the needle.

5. The method of claim 1 where the tool has an elongated body having a length of from 4 to 11 inches, said body including the handle section having a length of from 3 to 8 inches and an enlarged guard section having a length of from 0.5 to 3 inches, said guard section having a forward edge having a length of from 1 to 6 inches, said forward edge terminating at opposed ends in side edges which extend rearward to said handle section, said side edges having a length of from 0.5 to 3 inches, an elongated slot in the guard section which extends from the forward edge rearward towards said handle section and has a width of from 1/16 to 1/4 inch and a length of from 0.25 to 3 inches, said slot being at a right angle with respect to the forward edge, with the slot and the handle section being in substantial alignment with each other, both lying along a common longitudinal axis, the minimum distance between said slot and the side edges being 1 inch and the maximum distance between the slot and the side edges being 3 inch.

6. A method for manually inserting a needle into a medical device implanted under the skin of a patient, including (a) grasping with one hand a tool with a holder section and a handle section, and holding the tool by the handle section and pressing the holder section against the skin overlying the medical device, (b) gripping the needle with the other hand and inserting said needle through said skin into the medical device, and (c) maintaining the one hand a distance of at least three inches away from the needle as said needle is inserted into the medical device.

7. The method of claim 6 where said tool includes a handle section attached to the holder section, and said holder section has a pair of fork elements spaced apart a distance which is slightly greater than the width of the medical device.

8. The method of claim 6 where the fork elements are of equal length, each having a length of from 0.5 to 3 inch, and the holder section has a length of from 1.5 to 5 inches and the handle section has a length of from 3 to 8 inches.

9. The method of claim 6 where the tool is made from an injected molded polymeric material.

10. A method for manually inserting a needle into a medical device implanted under the skin of a patient, including (a) grasping with one hand a tool with a transparent holder section with an open section therein providing access to the patient's skin through which said needle is passed as said needle is inserted through said skin into the medical device, said guard section having indicia thereon for assisting in aligning the guard section with the implanted medical device, (b) gripping the needle with the other hand and inserting said needle through said skin into the medical device, and (c) aligning the guard section with the implanted medical device, using the indicia to bring the guard section into an overlying relationship with the implanted medical device with the open section being approximately over the central section of the implanted medical device, and (d) pressing the holder section against the skin overlying the medical device, covering the skin to maintain said one hand a safe distance away from the needle as said needle is inserted into the medical device.

11. The method of claim 10 where the tool includes an elongated body including a handle section and an enlarged guard section, said guard section having a floor made of a transparent material and having an area in excess of 1.25 square inches, said floor having a rear end to which the handle section is attached, opposed sides, and a forward edge, an elongated slot which extends from the forward edge rearward towards said handle section and terminates at an end at least 0.5 inches from the forward edge, said slot being substantially at a right angle with respect to the forward edge, with the slot and the handle section being in substantial alignment with each other, both lying along a common longitudinal axis, and said slot having between the forward edge and the end of the slot an enlarged open portion with an area in excess of 0.0036 square inch through which a needle is inserted when accessing the implanted medical device.

12. A tool for assisting in accessing and deaccessing a needle used with a medical device implanted under the skin of a patient, including an elongated body having a handle section and an enlarged guard section, said handle section and guard section being detachable, enabling the guard section to be discarded after use and said handle section being reusable, and an elongated slot extending from an edge of the guard section into the guard section, terminating at an internal portion of the guard section.

13. The tool of claim 12 where the guard section has an area of from 1.25 to 18 square inches.

14. The tool of claim 12 where said guard section is made of a transparent material.

15. The tool of claim 12 where the handle section has a length of from 3 to 8 inches.

16. The tool of claim 12 where the slot has a width of from 1/16 to 1/4 inch.

17. The tool of claim 12 where guard section has a smooth, generally planar underside surface.

18. The tool of claim 12 where the handle section has an elongated depression therein extending lengthwise along said handle section.

19. The tool of claim 12 where the handle section has a marker thereon indicating that a hand of the nurse should be behind said marker, said marker being a distance to position the hand of the nurse at least 3 inches away from the needle during use.

20. The tool of claim 12 where the slot has enlarged open portion with an area in excess of 0.0036 square inch through which a needle is inserted when accessing the implanted medical device.

21. The tool of claim 12 where there is a locking mechanism that engages the handle section upon inserting the handle section into a track on the guard section and a manually releasable element which upon being released allows the handle section to be detached from the guard section.

* * * * *